(12) United States Patent
Embrechts et al.

(10) Patent No.: US 8,362,087 B2
(45) Date of Patent: Jan. 29, 2013

(54) VETERINARY AQUEOUS INJECTABLE SUSPENSIONS CONTAINING FLORFENICOL

(75) Inventors: Erwin Embrechts, Hoogstraten (BE); Jan Embrechts, Hoogstraten (BE)

(73) Assignee: Calluna Pharma BVBA, Hoogsstraten (BE)

( * ) Notice: Subject to any disclaimer, the term of this patent is extended or adjusted under 35 U.S.C. 154(b) by 1685 days.

(21) Appl. No.: 10/566,356

(22) PCT Filed: Jul. 30, 2004

(86) PCT No.: PCT/EP2004/008587
§ 371 (c)(1),
(2), (4) Date: May 25, 2006

(87) PCT Pub. No.: WO2005/013959
PCT Pub. Date: Feb. 17, 2005

(65) Prior Publication Data
US 2006/0223889 A1  Oct. 5, 2006

(30) Foreign Application Priority Data
Jul. 31, 2003 (EP) .................................. 03017323

(51) Int. Cl.
*A01N 37/18* (2006.01)
*A01N 41/10* (2006.01)
*A01N 29/10* (2006.01)
*A61K 31/04* (2006.01)

(52) U.S. Cl. ......... 514/621; 514/709; 514/741; 514/751
(58) Field of Classification Search ................. 514/621, 514/709, 741, 751
See application file for complete search history.

(56) References Cited

U.S. PATENT DOCUMENTS

| 4,235,892 A | * | 11/1980 | Nagabhushan | ............... 514/522 |
| 5,646,151 A | * | 7/1997 | Kruse et al. | ..................... 514/13 |

FOREIGN PATENT DOCUMENTS

| EP | 0 014 437 A | 8/1980 |
| EP | 0 546 018 A | 6/1993 |
| WO | WO 98/41207 A | 9/1998 |
| WO | WO 02/41899 A | 5/2002 |

OTHER PUBLICATIONS

Mirza, Sabiruddin et al.; "Co-Crystals: An Emerging Approach for Enhancing Properties of Pharmaceutical Solids"; DOSIS vol. 24, Feb. 2008, pp. 90-96.

\* cited by examiner

*Primary Examiner* — Renee Claytor
(74) *Attorney, Agent, or Firm* — Dickstein Shapiro LLP

(57) ABSTRACT

This invention relates to pharmaceutical compositions for veterinary use in form of aqueous injectable suspensions comprising Florfenicol or Florfenicol in form of a substantially water-insoluble complex, co-crystal or salt, sterile and micronised, in a concentration up to 500 mg/ml. The suspensions enable parenteral antimicrobial therapies in animals, with limited numbers of injections and showing good general- and local tolerances. They also possess a limited sedimentation on standing as well as after shipping, are easily resuspendable and have good syringablity.

20 Claims, No Drawings

VETERINARY AQUEOUS INJECTABLE SUSPENSIONS CONTAINING FLORFENICOL

The invention relates to pharmaceutical compositions for veterinary use containing Florfenicol as the active pharmaceutical ingredient in high concentration, more specifically in aqueous injectable suspensions.

Florfenicol [D-(threo)-1-p-methylsulfonyl phenyl-2-dichloroacetamido-3-fluoro-1-propanol] is a known antibacterial agent which is commonly used for veterinary purposes. It is a broad-spectrum antibiotic that is active against many pathogenic veterinary bacteria (NEU et al., Antimicrob. Agents Chemother., 1980, 18, 2, 311-316; SYRIOPOULOU et al., Antimicrob. Agents Chemother., 1981, 19, 2, 294-297).

Injectable formulations containing Florfenicol are already described in several patents.

European Patent 0 014 437 B1 discloses not only the way of synthesis of Florfenicol, but also different formulation examples, including oral suspensions, injectable solutions in a water/dimethylacetamide mixture and sterile powders for extemporaneous reconstitution.

European Patent 0 546 018 B1 discloses a highly concentrated injectable formula for veterinary use. This injectable formula is based on a water-free combination of two different organic solvents. An additional viscosity reducing agent is required to enable the parenteral administration of this highly concentrated solution.

Although this formula is claimed to exhibit acceptable tissue tolerance at the injection site, practicing veterinarians designate its injection as very painful.

This injectable formula of European Patent 0 546 018 B1 might possibly be an improvement over former injectable solutions, e.g. formulations dissolved in pure N-Methyl-2-pyrrolidone, it still remains very irritating and painful, if compared to other physiologically acceptable aqueous solutions and suspensions, containing lower concentrations of physiologically acceptable solvents, with physiologically acceptable pH-values and distinctly less osmotic stress at the injection-site.

It is an object of the present invention to provide, highly concentrated aqueous injectable suspensions of the poorly water-soluble Florfenicol that can be manufactured with very good shelf life and stability, with a distinctly better local tolerance than the above mentioned injectable solutions, with short or sustained release serum levels for a long lasting antimicrobial activity after a reduced number of injections, and with limited sedimentation on standing, quick resuspendability on gentle shaking, even after shipping, and easy syringability on extraction.

Accordingly, the present invention relates to pharmaceutical compositions for veterinary use in the form of an aqueous suspension comprising Florfenicol or Florfenicol in the form of a substantially water-insoluble complex, co-crystal or salt, sterile and micronised, in a concentration up to 500 mg/ml.

With Florfenicol, such suspensions have not been available, so far.

In this context it shall be mentioned, that aqueous should be understood as essentially pure aqueous solutions without any further addition of organic solvents.

However it is evident, that these kinds of suspensions are not confined to injectable compositions. A further application in the form of stable, highly concentrated suspensions of Florfenicol, to be diluted into drinking water and animal-milk and/or milk replacers for veterinary use, appear also feasible.

In the following description of these formulations, all the concentrations of the ingredients mentioned are expressed in mg/ml.

Accordingly, the active ingredient Florfenicol is used in these aqueous suspensions in concentrations up to 500 mg/ml.

The Florfenicol raw material has to be sterile.

The Florfenicol raw material has to be micronised also, i.e. $\geq 95\%$ of the total volume of the Florfenicol raw material consists of particles with a particle size smaller than 200 µm, preferably smaller than 100 µm, more preferably smaller than 75 µm and most preferably smaller than 50 µm.

A likewise appropriate grade of micronisation has been obtained, when i.e. $\geq 90\%$ of the total volume of the Florfenicol raw material consists of particles with a particle size between 0.5 µm and 200 µm, preferably between 1 µm and 100 µm, more preferably between 1 µm and 75 µm and most preferably between 1 µm and 50 µm.

The grade of micronisation determines the shape of the Florfenicol serum curve in treated animals, viz.: the smaller the particles are, the faster the parenteral resorption occurs, but also the higher the tendency is of the suspension towards the detrimental "Ostwald ripening". Smaller particle sizes are used for treatments where high initial serum levels are required. Bigger particles are used for longer lasting serum levels. An equilibrated combination of both produces a serum curve with a bactericidal initial serum peak and a long lasting bacteriostatic serum slope for a long antimicrobial protection. So, the assortment of a well-equilibrated range out of this particle size distribution is a good method to provide a particular retardation of the active pharmaceutical ingredient, if required.

Micronisation of the particles should be conducted according to the state of the art, in dry form by means of a jet mill or in suspended form by means of a Co-Ball mill. The particles should preferably be non-acicular, but tabular for optimal resuspendability.

Well resuspendable aqueous suspensions contain a series of necessary excipients, viz.: buffers, suspending agents, surface-active agents, antioxidants and antimicrobial preservatives. Some of these constituents do flocculate the suspension, whereas others deflocculate them. The optimal equilibrium between flocculation and deflocculation has been established experimentally, with the aim to obtain suspensions with limited sedimentation on standing, quick resuspendability on gentle shaking, even after shipping, and easy syringability on extraction.

For an optimal chemical and physical stability of the suspension, the bulk solution needs to be buffered. Buffering components can be, but are not limited to: citric acid, ascorbic acid, isoascorbic acid, maleic acid, tartaric acid and boric acid and their respective hydrosoluble salts, monobasic and/or dibasic hydrogen phosphate, basic or acidic amino acids, such as arginine, cysteine, etc. and their hydrosoluble salts, as well as mixtures thereof. These buffer mixtures are present in concentrations from 1 mg/ml to 250 mg/ml, more preferably between 50 mg/ml and 250 mg/ml. It was observed that adequately buffering the injectable suspension, at the same time dramatically improves the local tolerance at the injection-site.

The pH of the bulk has to be within the range of physiological acceptance, which means between 3 and 9, more preferably between 5 to 8 and most preferably between 5 and 7.

The pH-value for optimal stability of Florfenicol in aqueous solution lies between 3 and 6. However, Florfenicol has a low solubility in water: at pH=7.0 it dissolves into water in a concentration of not more 1.3 mg/ml only, whereas Chloramphenicol dissolves in a concentration of 2.5 mg/ml.

Different suspending agents are used.

To equilibrate the floating density of the continuous phase and the repellent forces between adjacent particles, a sugar such as maltose, fructose and glucose but not limited thereto, a polyhydric alcohol such as sorbitol, mannitol and xylitol but not limited thereto, different kinds of glycols, such as glycerol, propylene glycol and polyethylene glycols but not limited thereto, sugar acids, uronic acids and/or fruit acids with at least 3 functional hydroxy and/or carboxy groups such as gluconic acid, heptagluconic acid, saccharic acid and citric acid but not limited thereto, and their water-soluble alkaline metal salts such as lithium, sodium, potassium, earth-alkaline metal salts such as magnesium and calcium salts and physiologically acceptable metal and transition metal salts such as aluminium, iron, manganese, zinc as well as their double salts can be added. Their concentration amounts from 10 mg/ml to 400 mg/ml, more preferably between 50 mg/ml and 300 mg/ml.

Dissolved in water, Florfenicol readily hydrolyses. Hence the first challenge of the galenical development of these Florfenicol suspensions consisted in keeping the suspended material as much as possible out of dissolution, by repelling its dissolution through the addition of sufficient amounts of readily hydrosoluble excipients. Increasing the concentrations of both the buffer mixtures and the suspending agents in the continuous phase noticeably reduced the degradation of Florfenicol.

For an optimal homogenisation of the floccules, sodium carboxymethylcellulose (Na-CMC) of low or medium viscosity grade can be added. It is used in a concentration of 0.1 mg/ml to 10 mg/ml. It increases the electrical charge of the particles in suspensions, up to its maximum value, which is mostly reached around a concentration of 5 mg/ml (POLDERMAN, Am. J. Hosp. Pharm., 1962, 19, 611-620).

Polyvinylpyrrolidone (PVP) is a non-ionizable compound that renders the suspension a better local tolerance at the injection-site. It however can enhance caking. To avoid caking and to improve resuspendability, the content of polyvinylpyrrolidone should be in equilibrium with the content of the sodium carboxymethylcellulose added. The amount of polyvinylpyrrolidone should be between 0.3 and 30 mg/ml, preferably between 1 and 10 mg/ml. Different polyvinylpyrrolidones with K-values between K 12 and K 32 can be used, but the ones with the lowest molecular weight are physiologically the most acceptable. In this way, polyvinylpyrrolidones with K-values from K 12 to K 15 are preferred.

The presence of a surface-active agent is necessary for two reasons: as a wetting agent for the particles to be suspended and for diminishing the risk of "Ostwald ripening", viz.: to suppress crystal growth during shelf life. These agents can be, but are not limited to: choline, phospholipids such as lecithins, non-ionogenic surface active agents, such as poloxamers, sorbitan fatty acid esters and polyoxyethylene sorbitan fatty acid esters, known under several commercial names, e.g.: spans and tweens, arlacels, crills and montanes. Lecithins are the preferred surface-active agents in the present suspensions. They consist of mixtures of phospholipids with different purity grades. The lecithins can be used in two different ways: either coated on the Florfenicol particles, in concentrations varying from 0.1 to 20 mg/ml, or dispersed into the continuous phase in concentrations from 0.1 to 50 mg/ml. Useful for that purpose are e.g. Lecithin brands Phospholipon® 90G, 90H and 100H from Nattermann Phospholipids GmbH, Köln. Other non-ionogenic surface-active agents can be used together with or instead of lecithins, e.g.: sorbitan esters or polyoxyethylene sorbitan esters in concentrations of 1 to 30 mg/ml.

Suspensions have to contain one or more water-soluble antioxidants and respective synergists. Useful antioxidants are sodium formaldehyde sulfoxylate, sodium metabisulphite, sodium phosphite, ascorbic acid, tartaric acid and cysteine, but not limited thereto, used alone or in combination, in concentrations of 0.1 to 40 mg/ml. Synergists potentiate the activity of these antioxidants. Useful synergists are: chelating or sequestering agents, such as citric and tartaric acid and especially sodium edetate and other edetic acid derivatives or the like. They are used in concentrations from 0.01 to 5 mg/ml.

Finally, the multi-dose injectable suspensions should be protected against microorganisms, possibly invading with contaminated injection needles, and hence have to meet the "Test for efficiency of antimicrobial preservation", adopted in the European Pharmacopoeia 4 "under 5.1.3-1 Parenterals". With that aim, they should contain one or more antimicrobial preservatives. Adequate and physiologically acceptable preservatives are, e.g. the parabens (methylparahydroxybenzoate, ethylparahydroxybenzoate, etc.), benzyl alcohol, chlorbutanol, phenoxyethanol, phenol and derivatives, quaternary ammonium compounds such as benzalkonium chloride and benzethonium chloride, benzoic acid, sorbic acid and their alkaline salts.

The suspensions of the present invention meet all the characteristics of good and reliable injectable suspensions, viz.: they show a limited sedimentation on standing as well as after shipping, a good resuspendability on gently shaking and a good syringability, even with thin needles.

The sedimentation height of the suspensions is investigated according to the method of WARD & KAMMERMYER, Ind. Eng. Chem., 1940, 32, 5, 622-626. It is expressed as the Hu/Ho-value, and amounts not less than 90% after 24 hours.

The resuspendabilty of the suspensions is measured according to the method of MATTHEWS & RHODES, J. pharm. Sci., 1968, 57, 569-573. After normal standing at room-temperature, the complete resuspendability is achieved after less than 10 rotations. Moreover, after a "shipping test" of 2000 km the suspensions can also easily be resupended on gentle shaking, and do not stick at the bottom of the vial.

The syringability of the suspension is expressed by means of the time needed to completely fill a 10 ml syringe, equipped with a 40 mm needle with diameter of 21 G (0.8 mm). At room-temperature, the syringability-time is less than 20 seconds.

The suspensions should be filled in siliconised sterile glass vials or sterile polyethylene or polypropylene vials, conceived for parenteral use, closed with sterile butylrubber stoppers and alu caps.

The following example describes the invention in general:

GENERAL EXAMPLE

| | |
|---|---|
| Active pharmaceutical ingredient, duly micronised | up to 500 mg/ml |
| Buffer mixture with pH between 5 and 8 | 1 to 250 mg/ml |
| Suspending agents: | |
| Sugars, polyhydric alcohols, glycols, sugar acids, uronic acids, fruit acids and their salts for equilibrating the floating density of the continuous phase and the repellent forces between adjacent particles | 10 to 400 mg/ml |

| | |
|---|---|
| Sodium CMC, low or medium viscosity grade | 0.1 to 10 mg/ml preferably ≦5 mg/ml |
| PVP | 0.3 to 30 mg/ml preferably 1 to 10 mg/ml |
| Surface active agents | |
| or: phospholipids coated on the particles | 0.1 to 20 mg/ml |
| dispersed in the continuous phase | 0.1 to 50 mg/ml |
| and/or: non-ionogenic surface active agents | 1 to 30 mg/ml |
| Antioxidants | 0.1 to 20 mg/ml |
| Antioxidant synergists | 0.01 to 3 mg/ml |
| Antimicrobial preservatives | |
| Water for injection | |

The following Examples describe the invention in detail:

Example 1

| | |
|---|---|
| Florfenicol micronised | 300 mg |
| Sodium citrate | 50.0 mg |
| Monopotassiumdihydrogenphosphate | 1.5 mg |
| Glucose monohydrate | 80.0 mg |
| Sodium CMC low viscosity | 2.0 mg |
| Polyvinylpyrrolidone K12 | 3.5 mg |
| Lecithin | 3.0 mg |
| Sodiumformaldehyde sulfoxylate | 2.5 mg |
| Sodium metabisulphite | 0.1 mg |
| Sodium edetate | 0.1 mg |
| Methylparaben | 1.0 mg |
| Propylparaben | 0.5 mg |
| Water for injection q.s. ad | 1 ml |

Example 2

| | |
|---|---|
| Florfenicol micronised | 250 mg |
| Sodium citrate | 50.0 mg |
| Sorbitol 70% | 250.0 mg |
| Sodium CMC medium viscosity | 0.8 mg |
| Polyvinylpyrrolidone K15 | 3.5 mg |
| Polysorbate 80 | 1.0 mg |
| Sorbitan monooleate | 1.0 mg |
| Sodiumformaldehyde sulfoxylate | 2.5 mg |
| Sodium phosphite | 10.0 mg |
| Sodium edetate | 0.1 mg |
| Benzyl alcohol | 9.0 mg |
| Water for injection q.s. ad | 1 ml |

Example 3

| | |
|---|---|
| Florfenicol micronised | 400.0 mg |
| Sodium citrate | 80.0 mg |
| Monopotassiumdihydrogenphosphate | 10.0 mg |
| Sodium gluconate | 150.0 mg |
| Sodium CMC low viscosity | 1.5 mg |
| Polyvinylpyrrolidone K12 | 3.5 mg |
| Lecithin | 3.0 mg |
| Sodiumformaldehydesulfoxylate | 2.5 mg |
| Sodium metabisulphite | 0.1 mg |
| Sodium edetate | 0.1 mg |
| Methylparaben | 1.0 mg |
| Propylparaben | 0.5 mg |
| Water for injection q.s. ad | 1 ml |

The invention claimed is:

1. Pharmaceutical composition for veterinary use comprising an aqueous injectable suspension comprising a concentration of up to 500 mg/ml sterile and micronised florfenicol or a substantially water-insoluble complex, salt thereof, said composition being free of organic solvents.

2. The composition of claim 1, wherein the florfenicol is present as such and more than 95% of the total volume of the florfenicol are particles with a particle size smaller than 200 μm.

3. The composition of claim 2 wherein the suspension has a continuous phase which contains 1 to 250 mg/ml of a buffer providing a pH-value in the range of 5 to 8.

4. The composition of claim 3 wherein the suspension contains 10 to 400 mg/ml of at least one stabilizer selected from the group consisting of a sugar, polyhydric alcohol, sugar acid, uronic acid and fruit acid having at least 3 functional hydroxy or carboxy groups or combination thereof, or a salt thereof.

5. The composition of claim 4, comprising 0.1 to 10 mg/ml of sodium carboxymethylcellulose.

6. The composition of claim 5, comprising 0.3 to 30 mg/ml of at least one injectable grade polyvinylpyrrolidone.

7. The composition of claim 6, comprising a phospholipid surface-active agent at a concentration of 0.1 to 50 mg/ml or at least one different non-ionogenic surface active agent at a concentration of 1 to 30 mg/ml, or both.

8. The compositions of claim 7, further comprising at least one antioxidant or synergist thereof, and antimicrobial preservative.

9. The composition of claim 8, disposed in an aseptically filled sterile primary packing material.

10. The composition of claim 9, wherein the phospholipid surface-active agent is disposed as a coating on the particles.

11. The composition of claim 10, wherein at least 90% of the volume of the particles have a particle size between 0.5 and 200 μm, the buffer is present in an amount of 50 to 250 mg/ml and provides a pH between 5 and 7, the amount of stabilizer is between 50 and 300 mg/ml, the amount of polyvinylpyrrolidone is between 1 and 10 mg/ml, and the amount of antioxidant or synergist thereof is between 0.1 and 40 mg/ml.

12. The composition of claim 11, wherein at least 90% of the volume of the particles have a particle size between 1 and 100 μm, and the polyvinylpyrrolidone has a K-value between K 12 and K 32.

13. The composition of claim 12, wherein at least 90% of the volume of the particles have a particle size between 1 and 50 μm, and the polyvinylpyrrolidone has a K-value between K 12 and K 15.

14. The composition of claim 13, disposed in an aseptically filled sterile primary packing material.

15. The composition of claim 1 wherein the suspension has a continuous phase which contains 1 to 250 mg/ml of a buffer providing a pH-value in the range of 5 to 8.

16. The composition of claim 1 wherein the suspension contains 10 to 400 mg/ml of at least one stabilizer selected from the group consisting of a sugar, polyhydric alcohol, sugar acid, uronic acid and fruit acid having at least 3 functional hydroxy or carboxy groups or combination thereof, or a salt thereof.

17. The composition of claim 1, comprising 0.1 to 10 mg/ml of sodium carboxymethylcellulose.

18. The composition of claim 1, comprising 0.3 to 30 mg/ml of at least one injectable grade polyvinylpyrrolidone.

19. The composition of claim 1, comprising a phospholipid surface-active agent at a concentration of 0.1 to 50 mg/ml, either coated on the particles or dispersed into the continuous phase or at least one different non-ionogenic surface active agent at a concentration of 1 to 30 mg/ml, or both.

20. The compositions of claim 1, further comprising at least one antioxidant or synergist thereof, and antimicrobial preservative.

* * * * *

UNITED STATES PATENT AND TRADEMARK OFFICE
CERTIFICATE OF CORRECTION

PATENT NO.      : 8,362,087 B2
APPLICATION NO. : 10/566356
DATED           : January 29, 2013
INVENTOR(S)     : Embrechts et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1859 days.

Signed and Sealed this
First Day of September, 2015

Michelle K. Lee
*Director of the United States Patent and Trademark Office*